(12) United States Patent
Wang et al.

(10) Patent No.: US 8,337,200 B2
(45) Date of Patent: Dec. 25, 2012

(54) HAND-HELD APPARATUS FOR CURING RESINS

(75) Inventors: Shan-Non Wang, Jhongli (TW); Chia-Ming Chang, Taoyuan (TW)

(73) Assignee: Rolence Enterprise Inc., Taoyuan County (TW)

( * ) Notice: Subject to any disclaimer, the term of this patent is extended or adjusted under 35 U.S.C. 154(b) by 294 days.

(21) Appl. No.: 12/757,711

(22) Filed: Apr. 9, 2010

(65) Prior Publication Data

US 2011/0248187 A1 Oct. 13, 2011

(51) Int. Cl.
*A61C 3/00* (2006.01)
(52) U.S. Cl. ......................... 433/29; 433/215; 250/492.1
(58) Field of Classification Search .................... 433/29, 433/315
See application file for complete search history.

(56) References Cited

U.S. PATENT DOCUMENTS

| | | | |
|---|---|---|---|
| 6,719,558 B2* | 4/2004 | Cao | 433/29 |
| 6,953,340 B2* | 10/2005 | Cao | 433/29 |
| 6,971,875 B2* | 12/2005 | Cao | 433/29 |
| 6,988,890 B2* | 1/2006 | Cao | 433/29 |
| 6,988,891 B2* | 1/2006 | Cao | 433/29 |
| 7,066,732 B2* | 6/2006 | Cao | 433/29 |
| 7,108,504 B2* | 9/2006 | Cao | 433/29 |

* cited by examiner

*Primary Examiner* — Nikita Wells
*Assistant Examiner* — Johnnie L Smith
(74) *Attorney, Agent, or Firm* — Houtteman Law LLC (57) ABSTRACT

A hand-held apparatus for curing resins includes a housing, a heat sink, a light-emitting unit, a power supply unit and a light transmission unit. The heat sink is installed in the housing. The light-emitting unit is installed on the heat sink. The light-emitting unit has at least one first light-emitting element for generating first wavelength light to cure the resins, at least one second light-emitting element for generating second wavelength light to generate white light, and at least one light-reflecting element surrounding the at least one first light-emitting element and the at least one second light-emitting element for reflecting the first wavelength light and the second wavelength light. The power supply unit provides power for the light-emitting unit. The light transmission unit is coupled to the housing for transmitting the first wavelength light and the second wavelength light to the resins.

12 Claims, 6 Drawing Sheets

HAND-HELD APPARATUS FOR CURING RESINS

BACKGROUND OF THE INVENTION

1. Field of the Invention

The present invention relates to a hand-held apparatus, and in particular to a hand-held apparatus that can illuminate different light sources to cure resins.

2. Description of Related Art

Hand-held apparatus is wildly used in many applications, for example, the curing hand-held apparatus is used to polymerize the curable material in dental practice.

Usually for a curing apparatus of hand-held size, at least one curing element for radiating light or heat is installed in the hand-held apparatus so that the byproduct of heat is built inside the apparatus to induce damage upon the electronic elements of the apparatus. Conventionally, there is a fan installed inside the apparatus for dissipating heat from the apparatus to the outsize environment via airflow exchange. However, the traditional hand-held apparatus cannot provide white light source to illuminate a target for viewing and positioning, and the traditional hand-held apparatus cannot provide many light sources at the same time to cure different types of resin.

SUMMARY OF THE INVENTION

In view of the aforementioned issues, the present invention provides a hand-held apparatus that can illuminate different light sources for aiming, viewing, positioning and curing different types of resin.

To achieve the above-mentioned objectives, the present invention provides a hand-held apparatus for curing resins, including: a housing, a heat sink, a light-emitting unit, a power supply unit and a light transmission unit. The heat sink is installed in the housing. The light-emitting unit is installed on the heat sink. The light-emitting unit has at least one first light-emitting element for generating first wavelength light to cure the resins, at least one second light-emitting element for generating second wavelength light to generate white light, and at least one light-reflecting element surrounding the at least one first light-emitting element and the at least one second light-emitting element for reflecting the first wavelength light and the second wavelength light. The power supply unit provides power for the light-emitting unit. The light transmission unit is coupled to the housing for transmitting the first wavelength light and the second wavelength light to the resins.

To achieve the above-mentioned objectives, the present invention provides a hand-held apparatus for curing resins, including: a housing, a heat sink, a light-emitting unit, a power supply unit and a light transmission unit. The heat sink is installed in the housing. The light-emitting unit is installed on the heat sink. The light-emitting unit has at least one first light-emitting element for generating first wavelength light to cure the resins, at least one second light-emitting element for generating second wavelength light to cure the resins, and at least one light-reflecting element surrounding the at least one first light-emitting element and the at least one second light-emitting element for reflecting the first wavelength light and the second wavelength light. The power supply unit provides power for the light-emitting unit. The light transmission unit is coupled to the housing for transmitting the first wavelength light and the second wavelength light to the resins.

To achieve the above-mentioned objectives, the present invention provides a hand-held apparatus for curing resins, including: a housing, a heat sink, a light-emitting unit, a power supply unit and a light transmission unit. The heat sink is installed in the housing. The light-emitting unit is installed on the heat sink. The light-emitting unit has at least one first light-emitting element for generating first wavelength light to cure the resins, at least one second light-emitting element for generating second wavelength light to cure the resins, at least one third light-emitting element for generating third wavelength light to generate white light, and at least one light-reflecting element surrounding the at least one first light-emitting element, the at least one second light-emitting element and the at least one third light-emitting element for reflecting the first wavelength light, the second wavelength light and the third wavelength light. The power supply unit provides power for the light-emitting unit. The light transmission unit is coupled to the housing for transmitting the first wavelength light, the second wavelength light and the third wavelength light to the resins.

Therefore, the present invention can illuminate different light sources for aiming, viewing, positioning and curing different types of resin according to different usage requirements.

In order to further understand the techniques, means and effects the present invention takes for achieving the prescribed objectives, the following detailed descriptions and appended drawings are hereby referred, such that, through which, the purposes, features and aspects of the present invention can be thoroughly and concretely appreciated; however, the appended drawings are merely provided for reference and illustration, without any intention to be used for limiting the present invention.

DETAILED DESCRIPTION OF THE PREFERRED EMBODIMENTS

Figure 1:
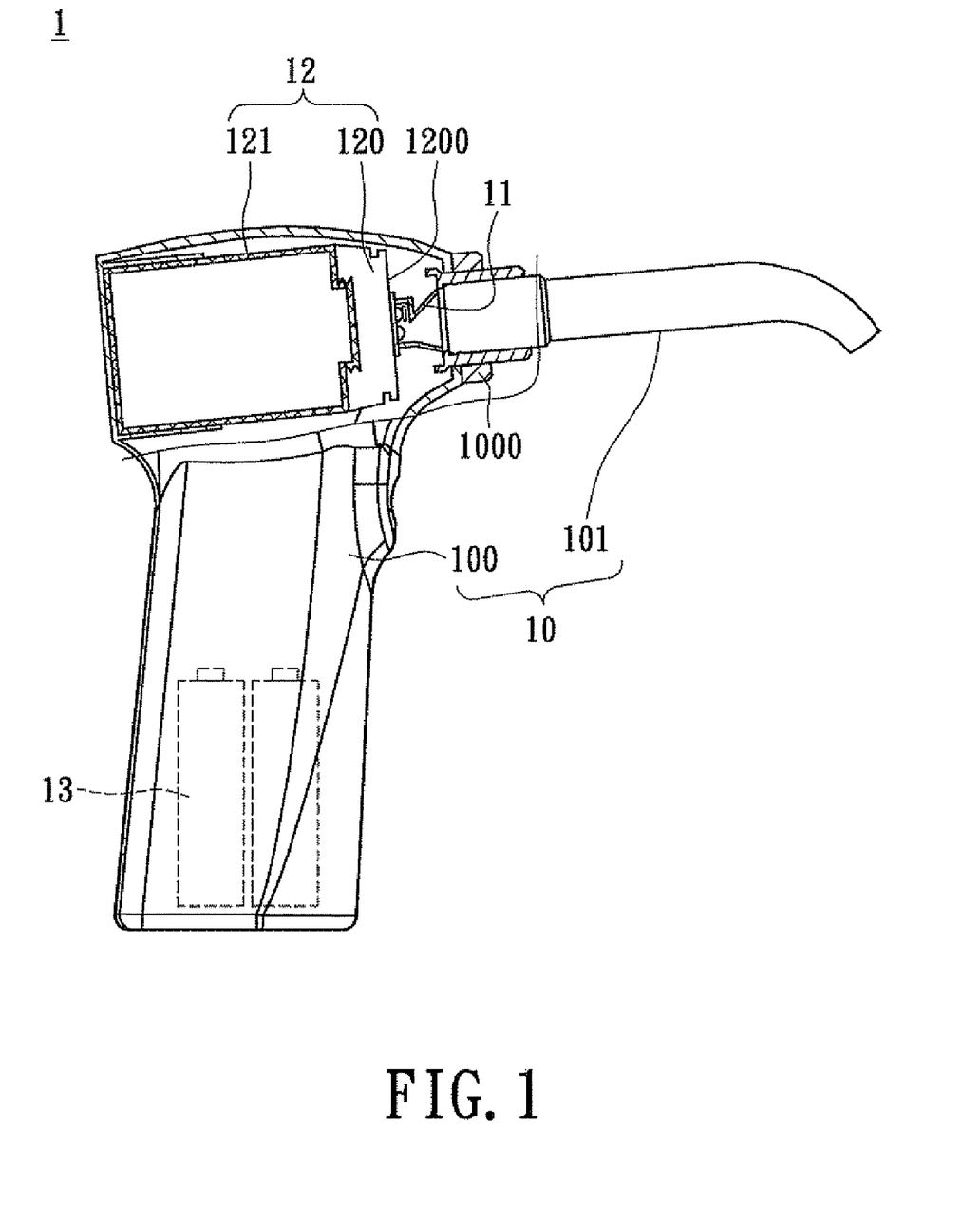
FIG. 1 is a schematic view of the hand-held apparatus according to the first embodiment of the present invention.
Figure 1A:
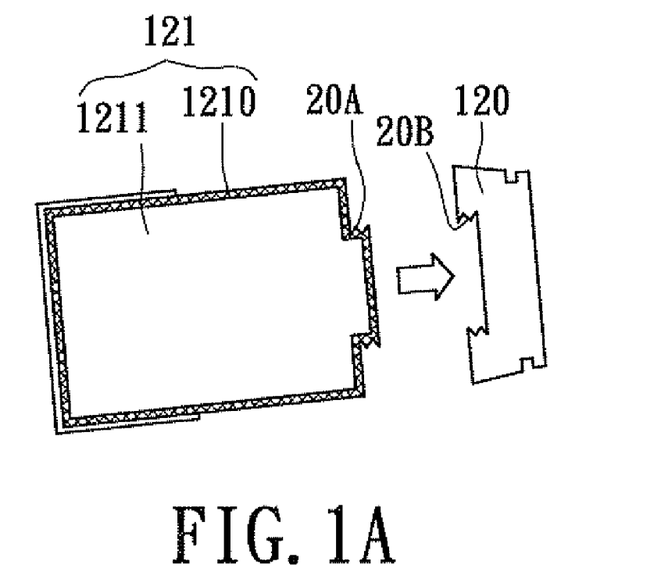
FIG. 1A is a schematic view of the first assembled type of mating the heat sink with the replaceable heat-dissipating module according to the first embodiment of the present invention.
Figure 1B:
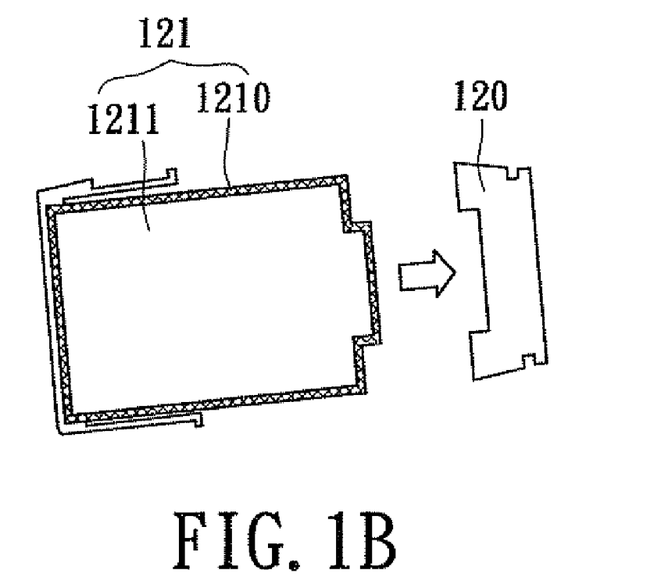
FIG. 1B is a schematic view of the second assembled type of mating the heat sink with the replaceable heat-dissipating module according to the first embodiment of the present invention.
Figure 1C:
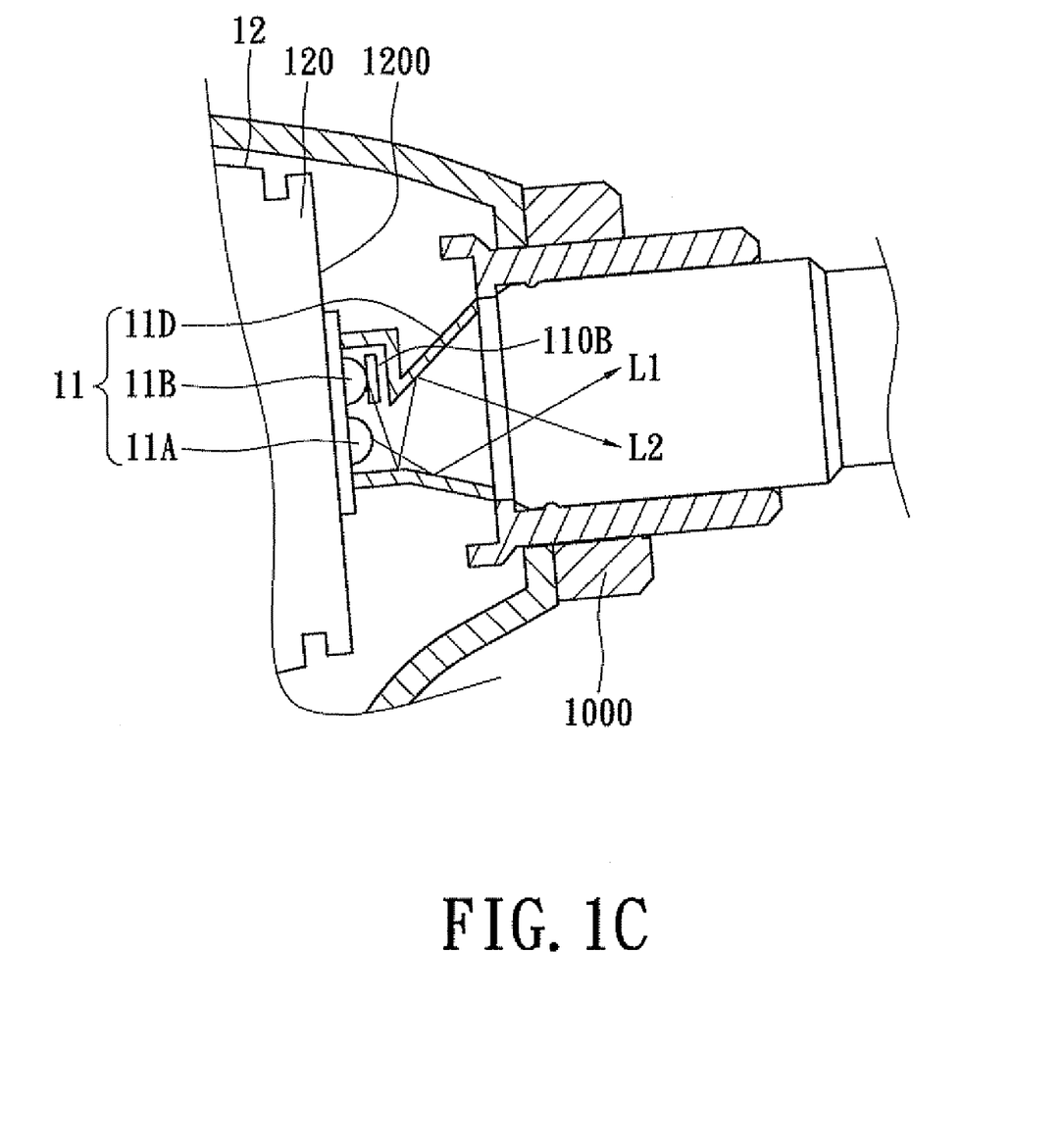
FIG. 1C is a partial enlarged view of the hand-held apparatus according to the first embodiment of the present invention.

Referring to FIGS. 1 to 1C, the present invention discloses a hand-held apparatus that is used for medical treatment application, especially in dental application for curing resins. The hand-held apparatus 1 comprises a housing 10, a heat sink 120 and a replaceable heat-dissipating module 121. The housing 10 defines a receiving space for containing components of the apparatus, and these components are described hereinafter. The heat sink 120 is installed inside the housing 10 and the replaceable heat-dissipating module 121 contacts tightly with the heat sink 120. The replaceable heat-dissipating module 121 is used for absorbing heat that is conducted from a light-emitting unit 11 through the heat sink 120. In other words, the heat sink 120 and the replaceable heat-dissipating module 121 are constructed as a heat-dissipating unit 12 with high heat-dissipating efficiency. FIG. 1A and FIG. 1B respectively shows a first and a second embodiments and the difference between the two embodiments are the locking means for combining the heat sink 120 and the replaceable heat-dissipating module 121.

FIGS. 1 and 1A show the first embodiment of the present invention. The replaceable heat-dissipating module 121 has a casing 1210 and liquid 1211 contained inside the casing 1210. The replaceable heat-dissipating module 121 can be drawn out from the heat sink 120 when the liquid 1211 has absorbed heats, and another new replaceable heat-dissipating module 121 can be put into the heat sink 120 for dissipating heat form the light-emitting unit 11.

The hand-held apparatus 1 provides radiation for curing compound in the embodiment, especially in, but not restricted to dental application. The hand-held apparatus 1 is usually used for short period of time. The hand-held apparatus 1 has a power supply unit 13 for the light-emitting unit 11 and the power supply unit 13 can be batteries or an AC/DC power converter. In other words, the heat-dissipating unit 12 of the present invention is suitable for hand-held instrument.

Referring to FIG. 1 again, the housing 10 of the hand-held apparatus 1 has a hand-held portion 100 and a light transmission unit 101. The hand-held portion 100 has an ergonomic shape for holding and the light transmission unit 101 is substantially a pipe. The hand-held portion 100 has an opening 1000 and a side of the light transmission unit 101 connects to the opening 1000. The other side of the light transmission unit 101 is away from the opening 1000. Moreover, the light transmission unit 101 can be a replaceable element and users can choose suitable light transmission unit 101 as desired by the required situations.

The heat sink 120 is installed in the housing 10 and the shape of the heat sink 120 is not restricted. Preferably, the replaceable heat-dissipating module 121 contacts closely to the heat sink 120 and a locking means is formed between the replaceable heat-dissipating module 121 and the heat sink 120. In the embodiment, the replaceable heat-dissipating module 121 is locked on the heat sink 120 so that the wall of the replaceable heat-dissipating module 121 can directly contacts the heat sink 120 for improving the heat-dissipating efficiency.

On the other hand, the casing 1210 of the replaceable heat-dissipating module 121 is made of metal materials with high conductivity and the liquid 1211 contained inside the casing 1210 is materials with high thermal capacity, such as water, saline water, or a mixture of water and antifreeze in order to store/absorb more heat.

The locking means for connecting the replaceable heat-dissipating module 121 with the heat sink 120 is described in detail. Referring to FIG. 1A, the locking means 20A and 20B are mated by screw threads. As to FIG. 1B, the locking means 20A and 20B are the clip mechanism at hand-held apparatus. The locking means has various types and the locking means is used for connecting the replaceable heat-dissipating module 121 with the heat sink 120.

Referring to FIGS. 1 and 1C, the hand-held apparatus 1 has a light-emitting unit 11 for projecting radiation to cure the curable compound. The light-emitting unit 11 is installed on the heat sink 120, for example on the outer surface of a side wall 1200 of the heat sink 120. The position of the light-emitting unit 11 corresponds to the opening 1000 of the hand-held portion 100. The light-emitting unit 11 has at least three aspects shown as follows:

The first aspect: referring to FIG. 1C, the light-emitting unit 1 has at least one first light-emitting element 11A (such as blue LED or ultraviolet LED) for generating first wavelength light L1 to cure the resins (not shown), at least one second light-emitting element 11B (such as white LED) for generating second wavelength light L2 to generate white light (the white light not only can be used to aim and view a target, but also can be used to cure resin), and at least one light-reflecting element 11D surrounding the at least one first light-emitting element 11A and the at least one second light-emitting element 11B for reflecting the first wavelength light L1 and the second wavelength light L2. In addition, the at least one first light-emitting element 11A is arranged on a center position of the light-emitting system of the present invention, and the at least one second light-emitting element 11B is disposed beside the at least one first light-emitting element 11A. Hence, user can use the second wavelength light (white light) L2 generated by the at least one second light-emitting element 11B to illuminate and aim the target such as medical resin first, and then using the first wavelength light L1 generated by the at least one first light-emitting element 11A to illuminate and cure the target. Furthermore, the first aspect further includes at least one diffusion sheet 110B disposed above the at least one second light-emitting element 11B for uniforming the second wavelength light L2. For example, the diffusion sheet 110E may be a sand-blasting glass.

Figure 2:
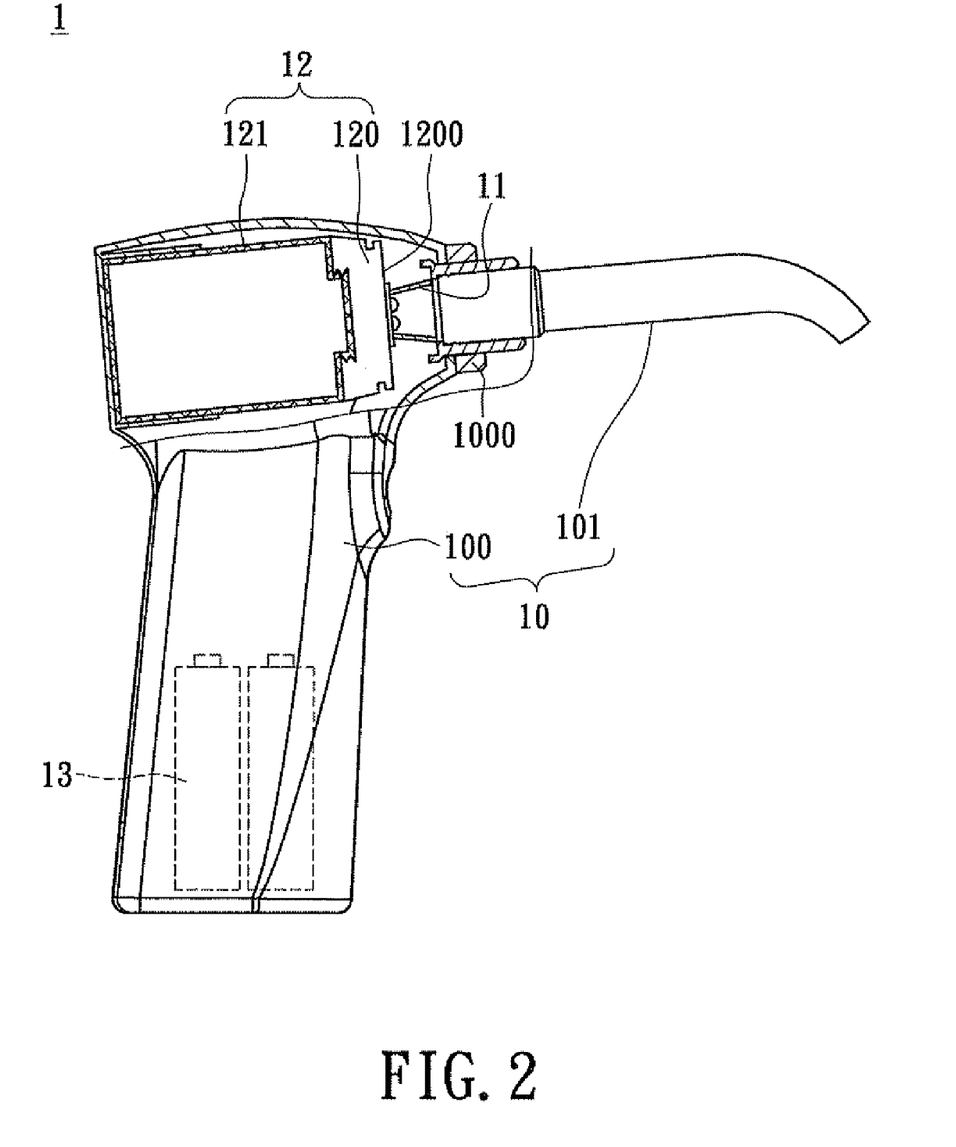
FIG. 2 is a schematic view of the hand-held apparatus according to the second embodiment of the present invention.
Figure 2A:
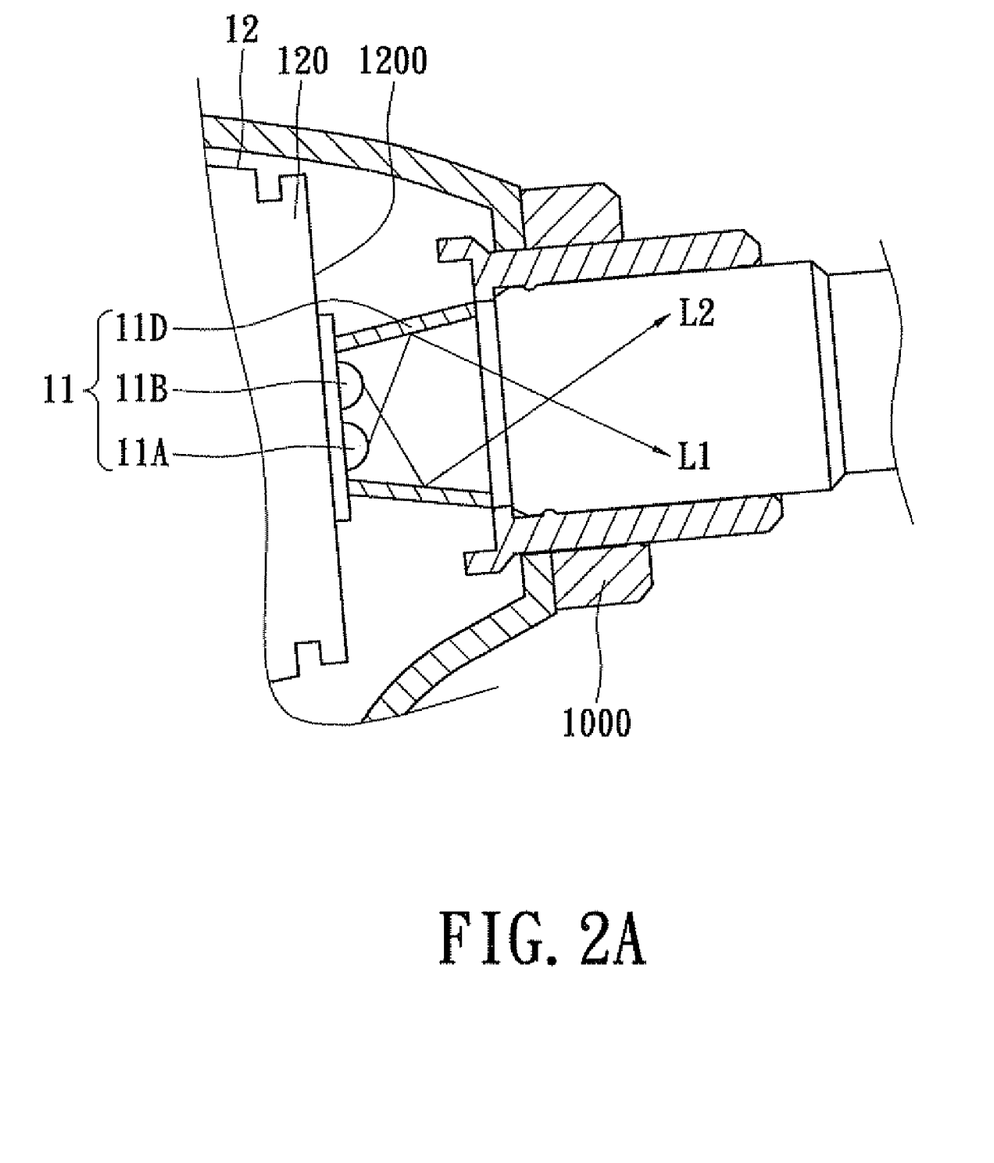
FIG. 2A is a partial enlarged view of the hand-held apparatus according to the second embodiment of the present invention.

The second aspect: referring to FIG. 2A, the light-emitting unit 1 has at least one first light-emitting element 11A (such as blue LED) for generating first wavelength light L1 to cure the resins (not shown), at least one second light-emitting element 11B (such as ultraviolet LED) for generating second wavelength light L2 to cure the resins (not shown), and at least one light-reflecting element 11D surrounding the at least one first light-emitting element 11A and the at least one second light-emitting element 11B for reflecting the first wavelength light L1 and the second wavelength light L2. Hence, user can selectively use (1) the first wavelength light L1, (2) the second wavelength light L2 or (3) the mixed light of mixing the first wavelength light L1 and the second wavelength light L2 to illuminate and cure the target.

Figure 3:
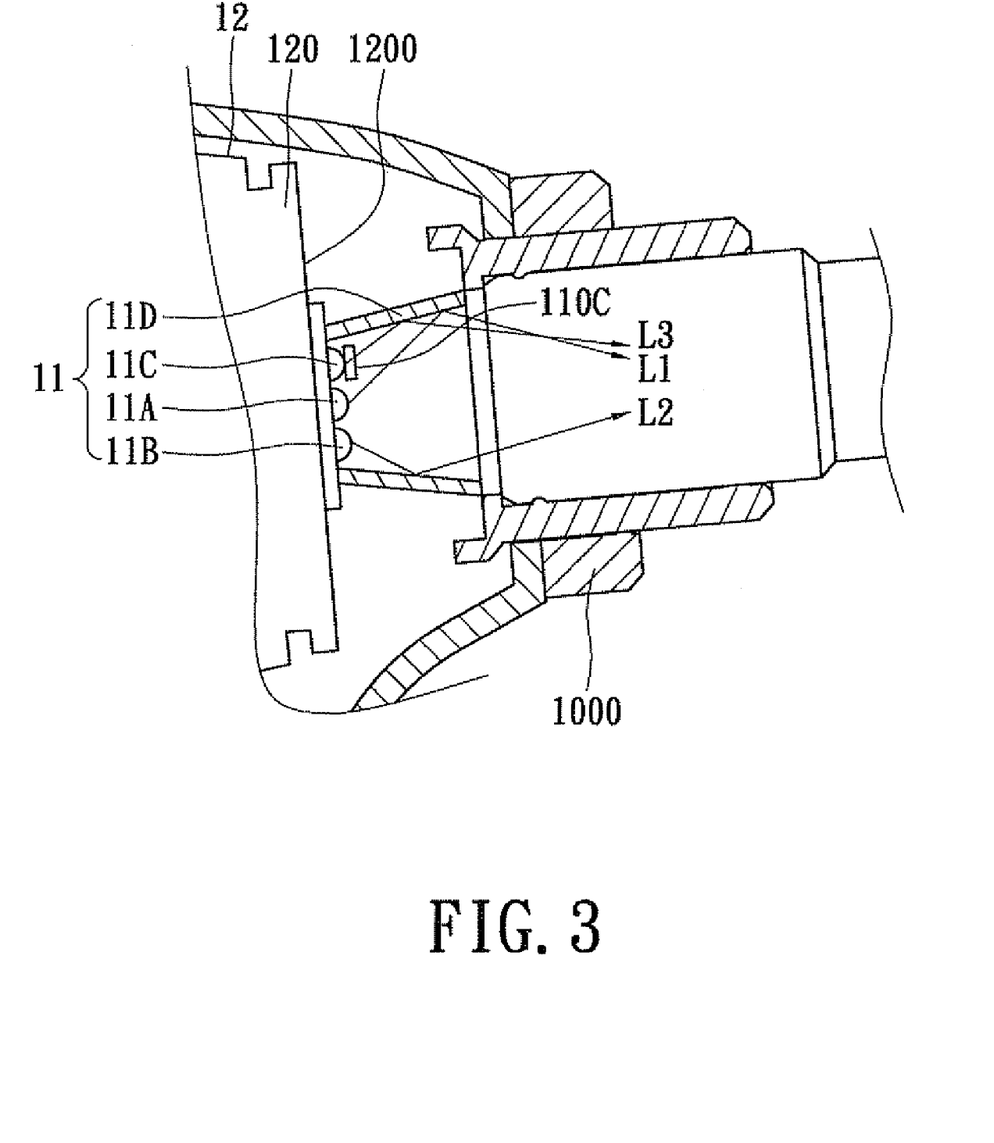
FIG. 3 is a partial enlarged view of the hand-held apparatus according to the third embodiment of the present invention.

The third aspect: referring to FIG. 3, the light-emitting unit 1 has at least one first light-emitting element 11A (such as blue LED) for generating first wavelength light L1 to cure the resins (not shown), at least one second light-emitting element 11B (such as ultraviolet LED) for generating second wavelength light L2 to cure the resins (not shown), at least one third light-emitting element 11C (such as white LED) for generating third wavelength light L3 to generate white light (the white light not only can be used to aim and view a target, but also can be used to cure resin), and at least one light-reflecting element 11D surrounding the at least one first light-emitting element HA, the at least one second light-emitting element 11B and the at least one third light-emitting element 11C for reflecting the first wavelength light L1, the second wavelength light L2 and the third wavelength light L3. Hence, the third aspect has the functions of the first aspect and the second aspect at the same time. Furthermore, the first aspect further includes at least one diffusion sheet 110B disposed above the at least one second light-emitting element 11B for uniforming the second wavelength light L2. For example, the diffusion sheet 110B may be a sand-blasting glass.

Furthermore, the hand-held apparatus 1 has a power supply unit 13 that electrically connects to the light-emitting unit 11 to supply the power for operation of the hand-held apparatus 1.

The position of the replaceable heat-dissipating module 121 can be adjusted for adapting the hand-held apparatus 1 to any application. For example, the replaceable heat-dissipating module 121 can be closed to the light-emitting unit 11 for dissipating heat more efficiently.

In usage, the light-emitting unit 11 is powered by the power supply of the power supply unit 13 to emit curing light and the light is transmitted to a predetermined curable materials though the light transmission unit 101. Simultaneously, the byproduct of heat is conducted to the replaceable heat-dissipating module 121 though the heat sink 120 and is absorbed within the liquid 1211. After the curable material is cured, the light-emitting unit 11 is powered-off. The replaceable heat-dissipating module 121 with stored heat can be drawn out and another replaceable heat-dissipating module 121 for absorbing heat can be connected with the heat sink 120 via locking means.

The replaceable heat-dissipating module 121 with stored heat can be placed under normal air condition for dissipating heat form the liquid 1211 to air. Alternatively, the replaceable heat-dissipating module 121 with stored heat can be placed into a refrigerator to dissipate faster the heat stored in the liquid 1211. Moreover, the housing 10 can have at least one venting hole thereon or not, under the condition that the electronic device inside the housing 10 can operate normally.

In conclusion, the present invention has some advantages shown as follows:

1. The present invention provides for an improved heat-dissipating efficiency. The heat is conducted away from the light-emitting unit via a solid path, i.e., the heat sink and the casing of the replaceable heat-dissipating module, and the conducted heat is stored within the liquid of high thermal capacity. Therefore, the byproduct of heat is dissipated from the light-emitting unit so that the performance of the light-emitting unit is not affected by the thermal increase.

2. Moreover, it is convenient for easily replacing the replaceable heat-dissipating module. The user can replace the replaceable heat-dissipating module while the hand-held apparatus is in non-operating period. In other words, when the hand-held apparatus is powered off, the replaceable heat-dissipating module with stored heat is replaced by a new one. Therefore, the heat is dissipated and stored within the liquid of the replaceable heat-dissipating module and the new replacement will not interrupt the curing process since it is faster to exchange the replaceable heat-dissipating module as suppose to wait for heat to dissipate on its own.

3. The replaceable heat-dissipating module is used for dissipating heat and the fans of prior art are omitted in the present invention. Therefore, the problems of fans, such as noise of fan operation and electric power consuming are solved.

4. The user can use the second wavelength light (white light) generated by the at least one second light-emitting element to illuminate and aim the target such as medical resin first, and then using the first wavelength light generated by the at least one first light-emitting element to illuminate and cure the target.

5. The user can selectively use (1) the first wavelength light L1, (2) the second wavelength light L2 or (3) the mixed light of mixing the first wavelength light L1 and the second wavelength light L2 to illuminate and cure the target.

The above-mentioned descriptions represent merely the preferred embodiment of the present invention, without any intention to limit the scope of the present invention thereto. Various equivalent changes, alternations or modifications based on the claims of present invention are all consequently viewed as being embraced by the scope of the present invention.

What is claimed is:

1. A hand-held apparatus for curing resins, comprising:
a housing having an opening;
a heat-dissipating unit including a heat sink disposed inside the housing;
a light-emitting unit disposed inside the housing to contact the heat sink, wherein the light-emitting unit has a substrate body, at least one first light-emitting element disposed on the substrate body and electrically connected to the substrate body, at least one second light-emitting element disposed on the substrate body and electrically connected to the substrate body, at least one light-diffusing sheet disposed on the at least one second light-emitting element, and a light-reflecting element disposed around the at least one first light-emitting element, the at least one second light-emitting element and the at least one light-diffusion sheet, wherein white light beams generated by the at least one second light-emitting element pass through the at least one light-diffusing sheet to form uniforming white light beams;
a power supply unit electrically connected to the at least one first light-emitting element and the at least one second light-emitting element; and
a light transmission unit connected to the opening of the housing and separated from the light-emitting unit.

2. The hand-held apparatus according to claim 1, wherein the light-diffusing sheet contacts the top side of at least one second light-emitting element, and the light-reflecting element disposed on the substrate body to surround the at least one first light-emitting element, the at least one second light-emitting element and the at least one light-diffusion sheet, wherein the heat-dissipating unit includes a replaceable heat-dissipating module filled with liquid, and the heat sink is disposed on the replaceable heat-dissipating module.

3. The hand-held apparatus according to claim 1, wherein the at least one first light-emitting element is a blue LED or an ultraviolet LED, and the at least one second light-emitting element is a white LED.

4. The hand-held apparatus according to claim 1, wherein the at least one light-reflecting element has at least one mirror with optical reflective property.

5. The hand-held apparatus according to claim 1, wherein the at least one light-reflecting element is a reflective plane with cup shape.

6. The hand-held apparatus according to claim 1, wherein the power supply unit is a battery or a power converter.

7. A hand-held apparatus for curing resins, comprising:
a housing having an opening;
a heat-dissipating unit including a heat sink disposed inside the housing;
a light-emitting unit disposed inside the housing to contact the heat sink, wherein the light-emitting unit has a substrate body, at least one first light-emitting element disposed on the substrate body and electrically connected to the substrate body, at least one second light-emitting element disposed on the substrate body and electrically connected to the substrate body, at least one third light-emitting element disposed on the substrate body and electrically connected to the substrate body, at least one light-diffusing sheet disposed on the at least one third light-emitting element, and a light-reflecting element disposed around the at least one first light-emitting element, the at least one second light-emitting element, the at least one third light-emitting element and the at least one light-diffusion sheet, wherein white light beams generated by the at least one third light-emitting element pass through the at least one light-diffusing sheet to form uniforming white light beams;

a power supply unit electrically connected to the at least one first light-emitting element, the at least one second light-emitting element and the at least one third light-emitting element; and a light transmission unit connected to the opening of the housing and separated from the light-emitting unit.

8. The hand-held apparatus according to claim 7, wherein the light-diffusing sheet contacts the top side of at least one second light-emitting element, and the light-reflecting element disposed on the substrate body to surround the at least one first light-emitting element, the at least one second light-emitting element and the at least one light-diffusion sheet, wherein the heat-dissipating unit includes a replaceable heat-dissipating module filled with liquid, and the heat sink is disposed on the replaceable heat-dissipating module.

9. The hand-held apparatus according to claim 7, wherein the at least one first light-emitting element is a blue LED, the at least one second light-emitting element is an ultraviolet LED, and the at least one third light-emitting element is a white LED.

10. The hand-held apparatus according to claim 7, wherein the at least one light-reflecting element has at least one mirror with optical reflective property.

11. The hand-held apparatus according to claim 7, wherein the at least one light-reflecting element is a reflective plane with cup shape.

12. The hand-held apparatus according to claim 7, wherein the power supply unit is a battery or a power converter.

* * * * *